United States Patent [19]
Balazs et al.

[11] Patent Number: 4,582,865
[45] Date of Patent: Apr. 15, 1986

[54] CROSS-LINKED GELS OF HYALURONIC ACID AND PRODUCTS CONTAINING SUCH GELS

[75] Inventors: Endre A. Balazs, Riverdale, N.Y.; Adolf Leshchiner, Fairview, N.J.

[73] Assignee: Biomatrix, Inc., Ridgefield, N.J.

[21] Appl. No.: 678,895

[22] Filed: Dec. 6, 1984

[51] Int. Cl.⁴ .............................................. C08F 8/00
[52] U.S. Cl. .................................... 524/29; 536/4.1; 524/27; 514/781
[58] Field of Search ............... 524/27, 29; 536/4.1

[56] References Cited

U.S. PATENT DOCUMENTS

| | | | |
|---|---|---|---|
| 3,357,784 | 12/1967 | Kasper | 8/129 |
| 4,141,973 | 2/1979 | Balazs | 536/55.1 |
| 4,303,676 | 12/1981 | Balazs | 424/359 |
| 4,487,865 | 12/1984 | Balazs et al. | 524/29 |
| 4,500,676 | 2/1985 | Balazs et al. | 424/81 |

Primary Examiner—Ronald W. Griffin
Attorney, Agent, or Firm—Sheldon Palmer

[57] ABSTRACT

Disclosed are cross-linked gels of hyaluronic acid, alone or mixed with other hydrophilic polymers and containing various substances or covalently bonded low molecular weight substances and processes for preparing them. These products are useful in numerous applications including cosmetic formulations and as drug delivery systems.

28 Claims, 2 Drawing Figures

EXAMPLE 3. SWELLING RATIO OF CROSS-LINKED HA GELS AT DIFFERENT CONCENTRATIONS OF HA IN STARTING SOLUTIONS (HA/DVS WEIGHT RATIO ABOUT 1:1, ROOM TEMPERATURE, 1 HOUR).

EXAMPLE 3. SWELLING RATIO OF CROSS-LINKED HA GELS AT DIFFERENT CONCENTRATIONS OF HA IN STARTING SOLUTIONS (HA/DVS WEIGHT RATIO ABOUT 1:1, ROOM TEMPERATURE, 1 HOUR).

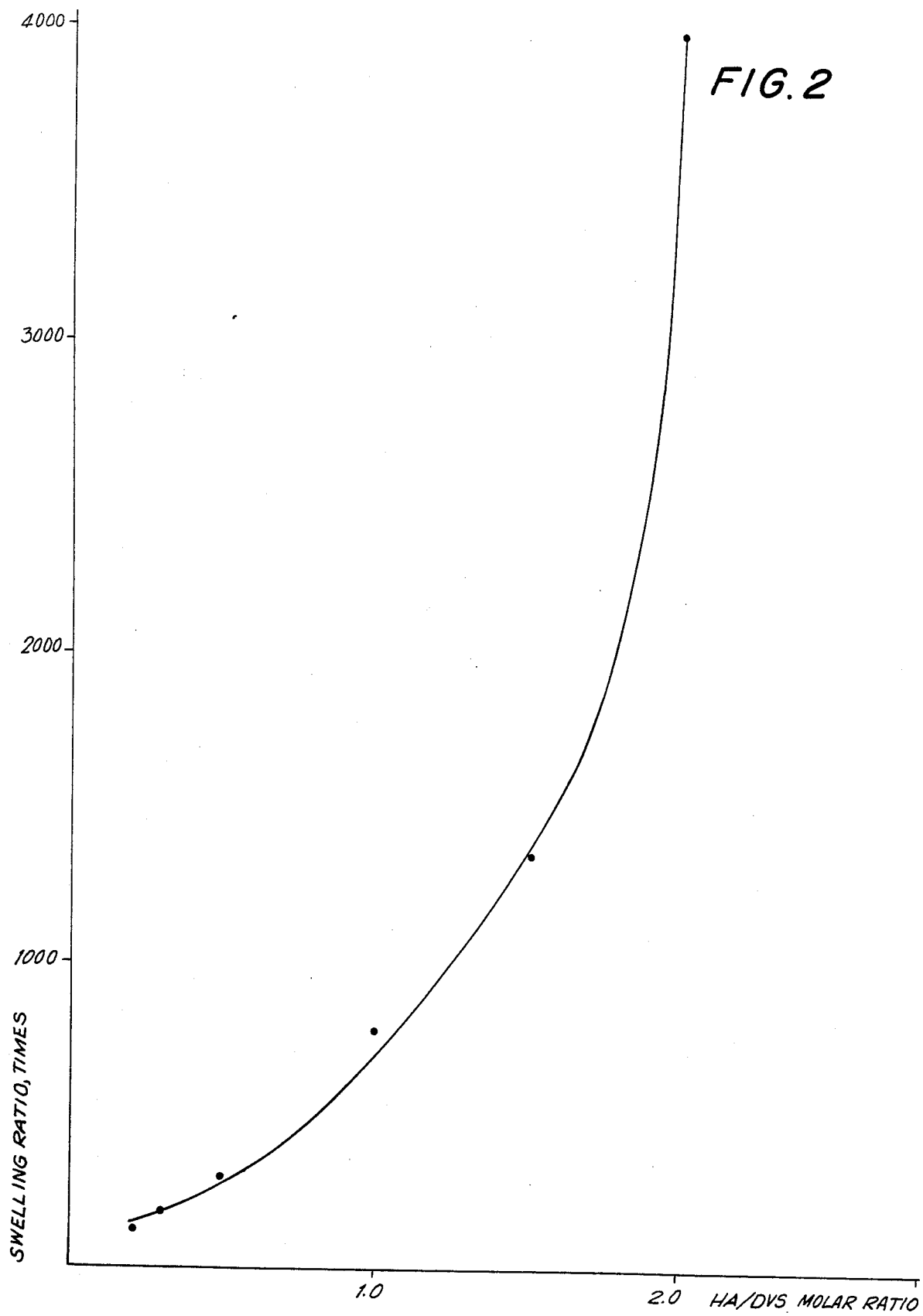
EXAMPLE 4. SWELLING RATIO OF CROSS-LINKED HA GELS AT DIFFERENT HA/DVS MOLAR RATIOS (HA CONCENTRATION IN STARTING SOLUTIONS 4 WT. %, ROOM TEMPERATURE, 1 HOUR).

CROSS-LINKED GELS OF HYALURONIC ACID AND PRODUCTS CONTAINING SUCH GELS

BACKGROUND OF THE INVENTION

1. Field of the Invention

The present invention relates to gels and mixed gels of hyaluronic acid (HA), formulations containing them and methods for preparing them.

2. The Prior Art

Hyaluronic acid is a well known, naturally occurring polysaccharide containing alternating N-acetyl-D-glucosamine and D-glucuronic acid monosaccharide units linked with $\beta 1 \rightarrow 4$ bonds and the disaccharide units linked with $\beta 1 \rightarrow 3$ glycoside bonds. Hyaluronic acid usually occurs as the sodium salt. The molecular weight of HA is generally within the range of 50,000 up to $8 \times 10^6$ and even higher.

The prior art describes the cross-linking of HA with the use of 1,2,3,4-diepoxybutane in alkaline medium at 50° C. (T. C. Laurent, K. Hellsing, and B. Gelotte, Acta Chem. Scand. 18 [1984], No 1, 274-5). The product obtained by that method is a gel which substantially swells in water.

It is also known that divinyl sulfone (DVS) is used for cross-linking polysaccharides, especially cellulose (U.S. Pat. No. 3,357,784).

BRIEF DESCRIPTION OF THE DRAWINGS

FIG. 2 is a graphical representation of the experimental data set forth in Example 4 below.

SUMMARY OF THE INVENTION

Figure 1:
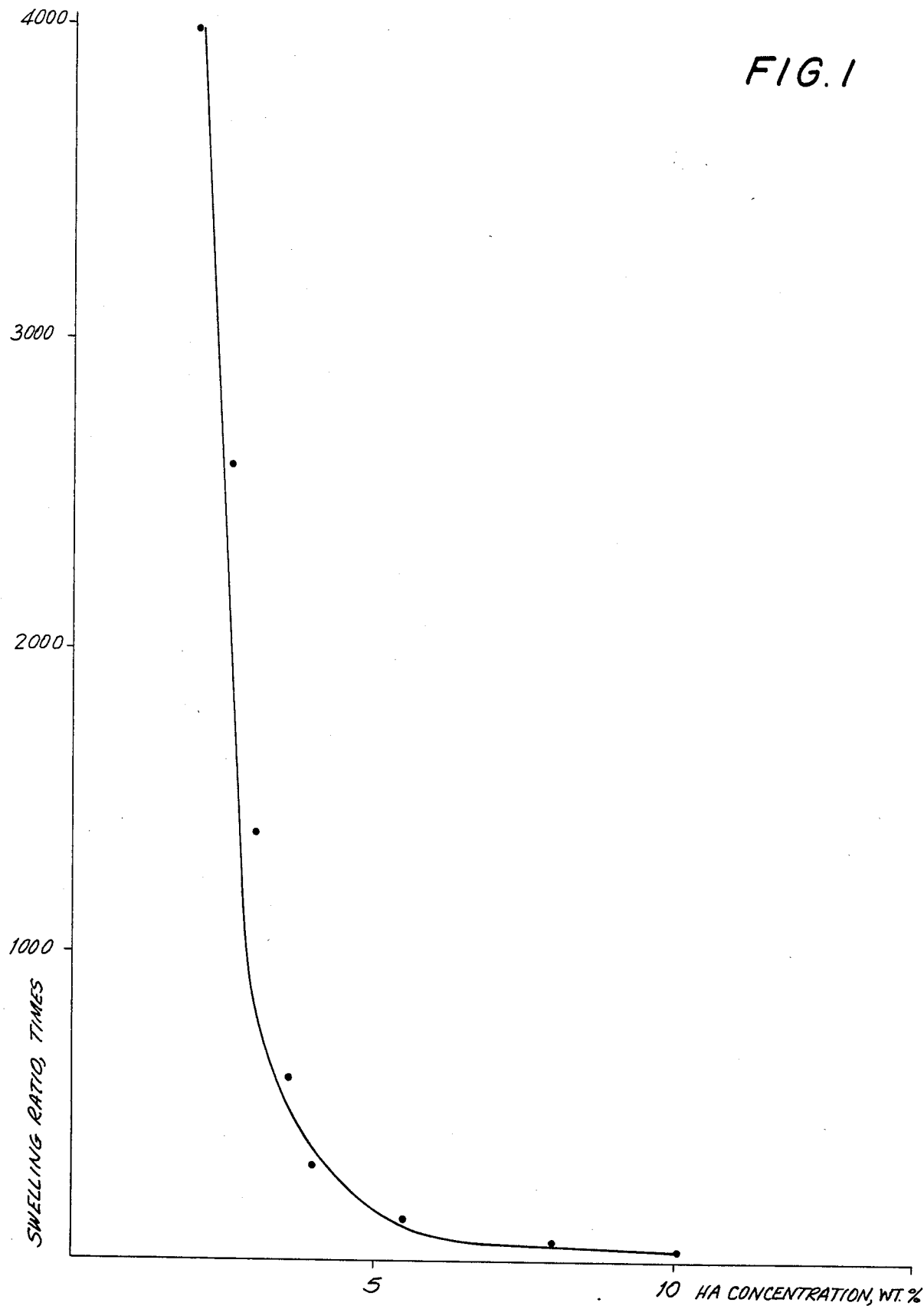
FIG. 1 is a graphical representation of the experimental data set forth in Example 3 below.

In one aspect thereof, the present invention provides highly swollen gels of cross-linked hyaluronic acid.

In another aspect, the invention provides mixed cross-linked gels of hyaluronic acid and other hydrophillic polymers.

In yet another aspect, the invention provides cross-linked gels of hyaluronic acid and other polymers filled with various substances.

In still another aspect, the invention provides cross-linked gels of hyaluronic acid containing low molecular weight substances covalently attached to the macromolecules.

In still yet another aspect, the invention provides various formulations containing cross-linked hyaluronic acid gels.

Finally, the invention provides the methods of preparing the products of the invention.

The present invention is based on the observation that divinyl sulfone (DVS) reacts readily with HA in aqueous alkaline solutions at room temperature, i.e., about 20° C., thereby providing cross-linked HA gels. As used herein, the term HA means hyaluronic acid and its salts such as the sodium, potassium, magnesium, calcium, etc. salts. These gels swell in water and water containing media. The swelling ratio depends upon the degree of cross-linking of the gel. We have found that the degree of cross-linking can be controlled by changing several factors including the molecular weight of the HA, its concentration in the reaction mixture, the alkali concentration and the polymer/DVS ratio. The reaction is very fast and in most cases a strong gel can be obtained in several minutes. The swelling ratio of these gels can be from 20 up to 8000, and more, depending upon the reaction parameters.

It has also been found that the swelling ratio of cross-linked HA gels is substantially greater than the swelling ratio of cross-linked gels of other polysaccharides obtained under the same reaction conditions. This can probably be explained by the unique nature of HA (as compared to other polysaccharides) and its water solutions. We have found that in water, a large molecule of HA forms a very flexible, long random coil which takes up an extremely large volume in the solution. For example, the specific volume of a hydrated HA molecule in a physiological salt solution is about $2-6 \times 10^3$ ml/g. That means that in a quite low concentration water solution of HA, a steric exclusion phenomenon occurs which will substantially affect not only the physicochemical properties of the solution, but the reaction of the HA with low molecular weight substances as well. In other words, the nature of the HA solutions affects the degree of cross-linking and the behavior of the cross-linked gel, in a manner quite unlike anything that occurs with other polysaccharides.

We have also found that this unique property of HA to give highly swollen cross-linked gels can be used to effect modification of the properties of cross-linked gels made of mixtures of HA with other hydrophillic polymers. These polymers include other polysaccharides, synthetic and natural, such as hydroxyethyl cellulose, carboxymethyl cellulose, xanthan gum, chondroitin sulfate, heparin, proteins of various types, such as collagen, elastin, albumin, a globulin, etc., sulfated proteins such as keratin sulfate and sulfated aminoglycosaminoglycans, synthetic water-soluble polymers, such as polyvinyl alcohol and its co-polymers, co-polymers of poly-(hydroxethyl)methacrylate and the like. In other words, any polymer soluble in water or water alkaline solutions and containing groups capable of reacting with DVS, namely, hydroxyl, amino or sulfyhydryl groups, can be used to obtain highly swollen cross-linked mixed gels of HA.

We have further found that useful products can easily be obtained by carrying out the cross-linking reaction of HA in the presence of low-molecular weight substances containing reactive groups of the mentioned types.

Another type of material according to the present invention is a cross-linked hydrophillic gel filled with various water insoluble substances including hydrocarbons, such as petrolatum; an oil or fat such as beeswax, conconut oil or lanolin, pigments, such as kaolin, ferric oxide; insoluble dyes, polymers, such as polyethylene, polyetrafluro ethylene, etc. In this type of product fine particles of a filler are immobilized in a gel network or in what we call a "polymer cage". This latter product can be very useful for several purposes which will be discussed in more detail below.

DESCRIPTION OF THE PREFERRED EMBODINEMT

The processes by which the hereinabove described products are obtained will now be discussed in detail.

In order to obtain a cross-linked HA gel, a sample of sodium hyaluronate or hyaluronic acid from any source is dissolved in dilute alkaline solution. The molecular weight of HA can be from 50,000 up to $8 \times 10^6$ and even higher. The molecular weight affects the reation—the higher the molecular weight the greater the possibility to obtain a cross-linked gel.

The alkali concentration in the reaction mixture can be from 0.005M to 0.5M and higher. The lower limit is dictated by the necessity to have the pH of the medium not lower than 9 and the upper limit by the hydrolysis of HA in an alkaline solution. Usually, a decrease in alkali concentration results in gels with a greater swelling ratio, probably because a small amount of DVS takes part in the cross-linking reaction.

The concentration of HA in the starting solution can vary from 1% by weight up to 8% by weight and higher. When the concentration is below the lower limit, a cross-linked gel cannot be obtained even at a low HA/DVS ratio. When the concentration is too high, the solution becomes so viscous that it is difficult to handle it. The HA concentration substantially affects the swelling behavior of the gels (FIG. 1). It was found that the shape of the curve for the swelling ratio—the HA concentration dependence is essentially the same for various HA/DVS ratios but the lower this ratio (i.e., more DVS in the mixture), the less the swelling ratio of the cross-linked gel for the same concentration of HA in the starting mixture.

We have found that HA/DVS in the reaction mixture is another parameter which can be conveniently used to control the swelling ratio of the cross-linked HA gel. An increase in the ratio results in highly swollen soft gels (the swelling ratio is about 4000 and higher) whereas hard and less swollen gels are obtained when this ratio is decreased. In general, the HA/DVS weight ratio can be from 15:1 to 1:5 and lower.

The cross-linking reaction is usually carried out at room temperature, i.e., about 20° C., but it can be performed at a lower or higher temperature, if desired. However, it should be kept in mind that HA can degrade relatively rapidly in alkaline solutions at elevated temperatures and, if such degradation occurs, the decrease in MW can affect the properties of the obtained gels.

The cross-linking reaction is relatively fast and strong gels are formed usually in several minutes when the HA concentration is high enough and the HA/DVS ratio is low. But even at low HA concentration in the reaction mixture, the gel formation starts usually 5–10 minutes after addition of DVS. We have found that in most cases one hour is enough for completion of the cross-linking reaction.

Another method of controlling the swelling ratio of cross-linked HA gels involves adding neutral salt to the reaction mixture. We have found that the swelling ratio of the gels obtained in the presence of water-soluble neutral salts, such as the chlorides, sulfates, phosphates and acetates of alkali metals, decreases with the increase of salt concentration. A salt can be used in concentration up to 20 wt. % and higher, depending upon the nature of the salt and its effect on the solubility of HA in the reaction mixture.

To obtained cross-linked gels of other hydrophillic polymers the same reaction conditions as for HA can be used. The swelling ratio of these gels can be conveniently controlled by incorporating HA into the gel structure. When the mixed gels are obtained, the composition of the polymer mixture can vary over a broad range depending on the swelling ratio of the cross-linked gel desired. The preferred content of HA in the mixture is from 5 to 95 wt. %.

Cross-linked gels of HA or other polymers or mixed cross-linked gels filled with inert substances are obtained by incorporating these substances into the reaction mixture before the addition of DVS. These inert substances are, preferably, water-insoluble liquids or solid substances. Examples of such substances are petrolatum and kaolin. To obtain a filled cross-linked gel, a chosen substance (based on a consideration of the desired properties of the gel) is emulsified or dispersed in an alkaline solution of HA or other polymer or mixture of HA with other polymer or polymers and DVS is added to the mixture. The amount of DVS and the other parameters of the reaction are selected depending upon the desired properties of the gel. The relative amount of filler in the gel can vary over a broad range and is from 1 to 95 wt. % calculated on the total amount of polymers and filler, preferably from 5 to 90 wt. %.

Cross-linked gels containing low molecular weight substances such as drugs, dyes and others covalently attached to the macromolecular network are obtained, preferably by incorporating the named substances into an HA or HA and other polymers solution before the addition of DVS. An example of such a substance is carminic acid, an FDA approved substance for use in food and drug preparations.

It is probably the presence of a glucosidic moiety of the carminic molecule which takes part in the cross-linking reaction with DVS. It should be understood that a great number of substances can be used to obtain a modified cross-linked gel of this type. The only essential feature of these substances is that they contain chemical groups with active hydrogen atoms reactive to DVS. The amount of such low molecular weight substances which can be used in the reaction depends upon the desired level of that substance in the gel. This amount can be in the range of from 1 to 99 wt. % as calculated on polymer content in the gel, preferably, 5 to 90 wt. %.

The cross-linked HA and mixed gels obtained according to the present invention can be used for many purposes. We have found that these highly swollen gels are very useful in cosmetic formulations and can be considered as water-retaining and water-delivering ingredients in these formulations.

As HA is known to be a biologically tolerable polymer in the sense that it does not cause any immune or other kind of response when introduced into a human body, the cross-linked HA gels can be used for various medical applications. The cross-linked gels modified with other polymers or low molecular weight substances can be used as drug delivery devices. For example, we have found that heparin introduced in a cross-linked HA gel retains its antithrombogenic activity.

We have also found that cross-linked gels of HA can slow down the release of a low molecular weight substance dispersed therein but not covalently attached to the gel macromolecular matrix.

The domain of the cross-linked hyaluronic acid (alone or co-polymerized with other polyanionic or neutral polymers) forms a molecular cage. In this cage, hydrophilic or hydrophobic molecules of various pharmacological or biological activity can be dispersed. Thus, the cage constitutes a depot for these substances of various molecular size. The substances contained in the domain of the molecular cage will be delivered into the environment by diffusion. The delivery process is controlled by such factors as the exclusion volume effect and the pore size of the molecular cage and by the molecular interaction between the polymeric network and the substance contained therein. Thus, the molecular cage forms a depot for the controlled delivery of drugs or other substances to the skin or other tissues.

There is one additional property of the cross-linked HA gels which makes them potentially very useful as drug delivery devices. The swelling ratio of these gels in water depends substantially upon the salt concentration in the medium and decreases several times with an increase in salt concentration. This means that a gel swollen in water will contract substantially when introduced into the body (because of the normal salt content of the body fluids and tissues), thus delivering its contents, i.e., an incorporated drug, into the body tissue.

The cross linked gels filled with various substances can also be used in cosmetic formulations. For example, a gel with petrolatum incorporated therein gives all the benefits of using petrolatum in cosmetic formulations without the unpleasant greasy feeling which is normally observed with petrolatum containing formulations.

DETAILED DESCRIPTION OF THE INVENTION

The present invention is described in more detail in the following examples, wherein all parts given are by weight unless otherwise indicated. These examples are given merely by way of illustration and are not intended to limit the invention as set forth in the claims.

EXAMPLE 1

This example illustrates the effect of varying HA molecular weight on the cross-linking reaction.

0.3410 g. of sodium hyaluronate obtained from rooster combs (intrinsic viscosity in 0.15M solution of NaCl $[\eta]$ 3850, MW about $2.5 \times 10^6$) was mixed with 8.1840 g. of 0.2M NaOH solution to give a 4% by weight solution after stirring for 30 minutes. Then, 0.0721 g. of DVS was stirred into the solution. The weight ratio HA/DVS was about 4.7. A strong gel formed in about 15 minutes. The gel was left for one hour and then put into one liter of distilled water. The gel was left to swell in water overnight. Then it was broken into small particles by vigorous stirring in water. The gel particles were filtered off and washed several times with water. Colorless, water clear particles were obtained. To determine the swelling ratio of the gel, a sample weighing about 1 g. was centrifuged in a glass filter at 3,000 rpm for two hours. Then the particles left on the filter were hydrolyzed with 2 ml of 1N $H_2SO_4$ solution for three hours at 95°–98° C. The clear solution obtained was neutralized upon cooling with 2 ml of 1N NaOH solution and the glucuronic acid content was determined by the carbazole method (An Automated Method For The Determination Of Hexuronic Acids, Analytical Biochemistry, 2, 517–558 [1965]). The HA content in the starting gel was calculated and the swelling ratio was expressed as 100/[HA]%, where [HA]% is a percent of HA in the swollen gel.

The swelling ratio in water of the gel obtained was 820.

This example was repeated with the exception that the solution of HA in alkali was kept at room temperature for 24 hours. This led to a HA hydrolysis. The intrinsic viscosity $[\eta]$ of the polymer was 1064 which corresponded to a MW of about $0.5 \times 10^6$. A cross-linked gel could not be obtained from this polymer at the HA/DVS ratio used above.

The example with the degraded HA was repeated but the HA/DVS ratio used was about 2. A cross-linked gel was obtained which had a swelling ratio in water of 2910.

EXAMPLE 2

This example illustrates the effect of alkali concentration on the cross-linking of HA.

A sample of HA with a MW of about $3 \times 10^6$ was dissolved in a calculated amount of 0.2M NaOH solution to give 4% viscous solution to which DVS was added in an amount providing an HA/DVS ratio of about 5:1. The cross-linking and treatment of the gel was carried out as described in the preceding example. The swelling ratio of the gel in water was 990.

The example was repeated but the alkali concentration was 0.01M. A gel was obtained with a swelling ratio in water of 3640. Thus, a decrease in the alkali concentration in the reaction mixture results in a gel with substantially greater swelling in water.

EXAMPLE 3

This example illustrates the effect of varying the HA concentration in the starting mixture on the swelling behavior of the resulting gel.

Eight solutions of sodium hyaluronate in 0.2M sodium hydroxide solution were prepared with the HA concentration being 2.0, 2.5, 3.0, 3.5, 4.0, 5.5, 8.0 and 10.0% by weight respectively. To each solution a calculated amount of DVS was added to have a weight ratio of HA/DVS about 1 (molar ratio about 0.33). The cross-linked gels were obtained as described in the above examples and treated accordingly. The swelling ratio was determined for each sample and plotted against starting HA concentration. The results are shown in FIG. 1.

EXAMPLE 4

This example illustrates the effect of varying the HA/DVS ratio on the swelling behavior of the resulting gel.

Six solutions of sodium hyaluronate in 0.2M sodium hydroxide solution were prepared with a concentration of 4.0% by weight. To each solution a calculated amount of DVS was added to have the following HA/DVS ratios: 0.2, 0.3, 0.5, 1.0, 1.5 and 2.0 mole/mole. The cross-linked gels were obtained and treated as described in the preceding examples. The swelling ratio was determined for each sample and plotted against HA/DVS ratio in the reaction mixture. The results are shown in FIG. 2.

EXAMPLE 5

This example illustrates the effect of sodium chloride in the reaction mixture on the swelling ratio of the cross-linked gel.

Two samples of the cross-linked HA gel were prepared with the use of the above described procedure. Sodium hyaluronate concentration in 0.2M sodium hydroxide was 4% by weight. The HA/DVS ratio was about 5:1, the reaction time one hour. To the second reaction mixture sodium chloride was added in an amount to have a 1.0 molar salt concentration. The swelling ratio of the first gel was 2380, whereas the gel obtained in the presence of salt had a swelling ratio in water of 650.

EXAMPLE 6

This example illustrates the cross-linking of hydroxyethyl cellulose with the use of DVS.

0.4312 g. of air-dry hydroxyethyl cellulose (Cellosize QP-100000 ®, Union Carbide) was dissolved with stirring in 10.3 g. of 0.2N sodium hydroxide to give 4% by weight. 0.0855 g. of DVS was stirred into this solution (polymer/DVS ratio was about 5:1 by weight) and the mixture was left for one hour at room temperature. A cross-linked gel was obtained which was processed as described in Example 1. To determine the polymer concentration in the gel and, hence, the swelling ratio, a weighed sample of the gel was put into acetone, kept overnight, washed several times with acetone and dried in a vacuum oven at 50° C. to a constant weight. The swelling ratio of the gel obtained was 43 which is substantially less than for cross-linked HA gel obtained under the same reaction conditions.

EXAMPLE 7

This example illustrates the cross-linking of xanthan gum with the use of DVS.

0.4935 g. of air-dry xanthan gum (Kelzan ®, Kelco) was dissolved in 11.3 g. of 0.2M sodium hydroxide solution to give a 4% by weight solution. To this solution 0.0718 g. of DVS was added (the polymer/DVS ratio was about 7:1 by weight). The mixture was kept for an hour at room temperature. The cross-linked gel finally obtained was put into a large volume of water, left to swell overnight and broken into small pieces which were extensively washed with water.

The swelling ratio of the gel determined by the weight method described in the preceding example was 526, which is substantially less than for cross-linked HA gel obtained under the same reaction conditions.

EXAMPLE 8

This example illustrates the cross-linking of a cationic water-soluble cellulose polymer with the use DVS.

0.5483 g. of a cationic cellulose polymer obtained by chemical modification of hydroxyethyl cellulose (Polymer Ucare JR ®, Union Carbide) was dissolved in 13.71 g. of 0.2M sodium hydroxide solution to give a 4% by weight solution to which 0.0849 g. of DVS was added (the polymer/DVS ratio was about 6.5:1). The reaction mixture was left to stand for an hour at room temperature and the gel obtained was processed and analyzed as described in the preceding example. The swelling ratio of the gel in water was 386, which is substantially less than that for a cross-linked HA gel obtained under the same reaction conditions.

EXAMPLE 9

This example illustrates the cross-linking of carboxymethyl cellulose with the use of DVS.

0.4703 g. of carboxymethyl cellulose sodium salt (9H 4F, Hercules) was dissolved in 11.76 g. of 0.2M NaOH to give a 4% by weight solution to which 0.0651 g. of DVS was added (the polymer/DVS ratio was about 7:1). The reaction mixture was kept for an hour at room temperature and the gel obtained was processed and analysed as described in the preceding example. The swelling ratio in water was 893, which is more than that obtained for other cellulosic polymers but less than for cross-linked HA gel.

EXAMPLES 10-13

These examples illustrate mixed cross-linked gels made of HA and carboxymethyl cellulose and the effect of the HA content on the swelling ratio of the gels.

In each example, sodium hyaluronate and carboxymethyl cellulose 9H4F were dissolved in 0.2M sodium hydroxide solution in such amounts as to provide specific ratios of the two polymers In all cases the total polymer concentration was 4% by weight and the polymer/DVS ratio was about 5:1. The gels were obtained and processed as described above. The polymer content in the gels was determined as described in Example 1, with the exception that the hexosamine concentration (instead of glucoronic acid) was determined by a known method (A Rapid Procedure for the Estimation of Amino Sugars on a Micro Scale, Analytical Biochemistry 15, 167–171 [1966]) in the hydrolyzate. The polymer content was calculated from the HA concentration and the ratio of the two polymers.

|  | HA Content in the Starting Mixture, Wt. % | Swelling Ratio in Water |
|---|---|---|
| Example 10 | 70 | 8196 |
| Example 11 | 50 | 6757 |
| Example 12 | 20 | 1117 |
| Example 13 | 0 | 623 |

As can be seen from these data, an increase in the HA content in the starting mixture results in an increase in the swelling ratio of the resulting gels.

EXAMPLE 14

This example illustrates mixed cross-linked gels obtained from HA and collagen. 0.2531 g. of dry sodium hyaluronate was dissolved in 2.5 ml of 0.1M sodium hydroxide solution. 0.063 g. of collagen obtained from human umbilical cord was dissolved in 2.3 ml of 0.1M acetic acid and the two solutions were combined. The total polymer concentration was 6 wt. % and the weight ratio HA/collagen was about 4:1. 0.05 g. of dry KCl was dissolved in the mixed solution and DVS was stirred into the reaction mixture in an amount providing a polymer/DVS ratio of about 5:1. The reaction mixture was kept at room temperature for an hour and the gel obtained was treated as described above. The polymer content in the swollen gel was calculated from the HA content which was found by the glucuronic acid assay. A strong and resilient gel was obtained which had a swelling ratio in water of 321.

EXAMPLE 15

This example illustrates a mixed cross-linked HA-collagen gel with a higher content of collagen and a lower swelling ratio than the gel described in Example 14.

0.2544 g. of sodium hyaluronate was dissolved in 3.5 ml of 0.2M sodium hydroxide solution. 0.1192 g. of collagen obtained from human umbilical crod was dissolved in 1.5 ml of 0.2M acetic acid solution and the solutions were combined. The total polymer concentration was 7.5 wt. % and the weight ratio HA/collagen was about 2:1. 0.05 g. of sodium chloride was dissolved in the mixed solution to which 0.1189 g. of DVS was added, thus providing a polymer/DVS ratio of about 3:1 by weight. The gel was obtained and processed as described in the preceding example. A strong gel was obtained with a swelling ratio of 35.

EXAMPLE 16

This example illustrates a mixed cross-linked gel of HA and heparin.

0.2968 g. of dry sodium hyaluronate was dissolved in 6.92 g. of 0.2M sodium hydroxide solution to give a 4 wt. % solution to which 0.0503 g. of heparin was added. The heparin content calculated on the basis of the total amount of polymers was 14.5 wt. %. 0.0590 g. of DVS was stirred into the mixture. The reaction was carried out for an hour at room temperature. The obtained gel was processed as described in the preceding examples. The swelling ratio of the gel was 625.

EXAMPLE 17

This example illustrates a cross-linked hydroxyethyl cellulose gel filled with petrolatum.

0.5292 g. of dry hydroxyethyl cellulose was dissolved in 10.58 g. of 1M sodium hydroxide solution and 1.058 g. of white petrolatum was stirred into the solution. The petrolatum/polymer ratio was about 2. A solution of 0.1771 g. of DVS in 1.0 g. of 1M sodium hydroxide solution was added to the emulsion with vigorous stirring. The reaction mixture was left for an hour at room temperature and the gel obtained was treated as described in the above examples. To find the petrolatum content in the gel, a gel sample was digested with 2 ml of 1N $H_2SO_4$ at 95° C. for three hours. Then 2 ml of 1N NaOH was added to the mixture followed by 4 ml of xylene to extract the petrolatum. The extract was dried off in vacuum and the residue was weighed. The calculated petrolatum content in the gel was 6 wt. %.

EXAMPLE 18

This example illustrates a mixed HA-carboxymethyl cellulose gel filled with petrolatum.

0.1830 g. of dry sodium hyaluronate and the same amount of carboxymethyl cellulose were dissolved in 9.1 g. of 0.2N sodium hydroxide solution to give a 4 wt. % solution of polymer. 0.3660 g. of petrolatum was stirred into the solution and 0.0730 of DVS was added to the resulting emulsion with vigorous stirring. The polymer/DVS ratio was about 5:1. The reaction mixture was left for an hour at room temperature. The obtained gel was processed as described in the preceding example. The swelling ratio of the gel determined through hexosamine content was 738 and the petrolatum content determined as in the preceding example was 0.1 wt. %.

EXAMPLE 19

This example illustrates a cross-linked HA gel filled with kaolin.

0.2700 g. of dry sodium hyaluronate was dissolved in an amount of 0.2N sodium hydroxide solution sufficient to obtain a 4 wt. % solution of the polymer. 0.5400 g. of kaolin was stirred into the solution. 0.0540 g. of DVS was added to the suspension and the reaction mixture was left for an hour at room temperature. The gel formed was left to swell in a large volume of water. The highly swollen gel was broken into small particles by pushing it through a syringe with a needle. The particles were extensively washed with water. Milky white, highly swollen particles were obtained. The concentration of solids in the gel was 0.064 wt. %.

EXAMPLE 20

This example illustrates a cross-linked HA gel containing carminic acid covalently attached to the macromolecular network.

0.20 g. of dry sodium hyaluronate and 0.04 g. of carminic acid were dissolved in 5.0 ml of 0.2M sodium hydroxide solution to give an approximately 4 wt. % solution of polymer. 0.40 g. of DVS was added to the solution (polymer/DVS ratio was 1:2) and the mixture was left for an hour at room temperature. The gel obtained was processed as described in the preceding examples.

Red colored transparent gel particles were obtained and the color did not disappear after extensive washing with water. The swelling ratio in water determined by the weight method was 115.

EXAMPLE 21

This example illustrates the effect of salt concentration in water on the swelling behavior of a cross-linked HA gel.

A cross-linked HA gel was obtained as described in the preceding examples with an HA concentration in 0.2M NaOH of 4 wt. %; HA/DVS ratio 5:1, at room temperature for one hour. The gel particles were put into water and aqueous sodium chloride solution of different concentrations and the swelling ratios were determined. The following results were obtained:

| NaCl Concentration, M | Swelling Ratio |
| --- | --- |
| Water | 990 |
| 0.05 | 413 |
| 0.15 | 384 |
| 0.50 | 219 |
| 1.00 | 176 |

EXAMPLE 22

This example illustrates the biological activity of a mixed HA-heparin cross-linked gel.

Fine particles of the mixed HA-heparin cross-linked gel prepared according to Example 16 were mixed with normal human plasma in amounts providing concentrations of cross-linked HA of 0.01, 0.02 and 0.04% and the clotting time of the samples increased respectively by 1.4, 2.8 and 5.0 times. Identical concentrations of non-heparin containing, cross-linked gel particles had no effect on clotting time.

These data indicate that heparin does not lose the ability to inhibit thrombin-catalyzed fibrin formation when it is incorporated into a cross-linked gel structure.

EXAMPLE 23

This example illustrates a product containing cross-linked HA gel particles useful for cosmetic formulations.

A cross-linked HA gel was prepared as described in Example 1 under the following reaction conditions: HA concentration 3.0 wt. %, sodium hydroxide concentration 0.2M, HA/DVS ratio about 3:1, room temperature, time one hour. The gel was allowed to swell in a large volume of water overnight, then was broken into small particles by pushing through a syringe with a needle of 18½ gauge and then through a syringe with a needle of 25½ gauge. The particles were thoroughly washed with water. Optically clear, colorless particles were obtained. the swelling ratio of the gel was 1980. The HA concentration of the filtered gel particles was 0.025 wt. %. These particles were used in mixtures with high molecular weight polyethylene oxide (Polyox ® Coagulant, Union Carbine) and soluble sodium hyaluronate (Hyalderm ®, Biomatrix, Inc.) of the following composition:

| Ingredients | Parts By Weight: | | |
|---|---|---|---|
| | Mixture 1 | Mixture 2 | Mixture 3 |
| Cross-linked gel | 90 | 80 | 75 |
| Hyladerm ® (1% solution of sodium hyaluronate) | 5 | 2 | 14 |
| Polyox ® 1% solution in water | 5 | 4 | 11 |
| Water | — | 14 | — |

All of these formulations had the appearance of homogeneous viscous liquids even though they were heterogeneous by the nature of the ingredients. When appled to the skin they gave a very soft, silky feel.

EXAMPLE 24

This example illustrates a moisturizing eye cream containing a cross-linked HA gel according to the present invention.

| | % By Weight |
|---|---|
| A. Carbopol ® 940 (B. F. Goodrich) | 0.4 |
| Mixture #3 (Example 23) | 10.0 |
| Water | 83.3 |
| B. Volpo ® -3 (Croda, Inc.) | 1.0 |
| Volpo ® -5 (Croda, Inc.) | 0.5 |
| Solulan ® C-24 (Amerchol Co.) | 1.8 |
| Roban ® | 1.0 |
| Crodamol ® PMP (Croda, Inc.) | 0.5 |
| Glucam ® E-10 (Americhol) | 0.7 |
| Preservative | 0.3 |
| C. Triethanolamine | 0.4 |
| Fragrance | 0.1 |

This formulation is prepared in separate stages, as follows: Part A of the mixture was prepared by dispersing the Carbopol ® in water and then stirring in the other components. All the part B components were mixed together and heated to 70° C. Parts A and B were then combined and the triethanolamine and fragrance were added. The resulting cream was stable and smooth and had good moisturizing qualities and an excellent feel on the skin.

EXAMPLE 25

This example illustrates the use of the petrolatum filled cross-linked gel in a hand lotion.

| | % By Weight |
|---|---|
| A. Carbopol ® | 0.25 |
| Carboxymethylcellulose 9H4F, 1% water solution | 2.00 |
| Product of Example 18 | 60.00 |
| Water | 36.70 |
| B. Robane ® | 0.20 |
| Cochin ® | 0.10 |
| Preservative | 0.30 |
| C. Triethanolamine | 0.25 |
| Fragrance | 0.20 |

This formulation was prepared as the one described in the preceding example. The resulting lotion was rich with excellent moisturizing qualities and did not give a greasy feeling on the skin.

The ingredients noted in Examples 24 and 25 by trademark are identified as follows:

| | |
|---|---|
| Volpo-5 ® | Oleth-5 (polyethylene glycol ether of oleyl alcohol) |
| Volpo-3 ® | Oleth-3 (polyethylene glycol ether of oleyl alcohol) |
| Solulan ® C-24 | Choleth-24 (polyethylene glycol ether of Cholesterol) |
| Crodamol ® PMP | (propoxylated myristyl propionate) PPG-3 Myristyl Ether Propionate |
| Glucam ® E-10 | Methyl gluceth-10 (polyethylene glycol ether of methyl glucose) |

EXAMPLE 26

This example illustrates the slow release of a low molecular weight substance dispersed in a matrix of cross-linked hyaluronic acid.

In this experiment, a radioactive labelled substance, hydroxytryptamine binoxolate, 5-[1,2-$^3$H(N)]-, was used. 5 μl of a 40 μM solution of the substance was mixed with 5 μl of cross-linked HA gel particles (HA concentration in the gel 0.131%) and water, respectively. The mixtures were put into dialysis tubes and dialyzed against 0.15M NaCl solution for 24 hours. For the mixture of the labelled substance and the cross-linked gel, 54% of the starting amount of the labelled material was left in the dialysis tube, whereas only 10% remained for the water solution. This demonstrates that the cross-linked gel of HA slows down the release of the low molecular weight substance by a factor of more than 5 times.

Variations and modifications can, of course, be made without departing from the spirit and scope of the invention.

Having thus described our invention what we desire to secure by Letters Patent and hereby claim is:

1. A method of preparing a mixed cross-linked gel of hyaluronic acid and at least one other hydrophilic polymer having a functional group capable of reacting with divinyl sulfone, said method comprising subjecting a mixture of sodium hyaluronate and said other hydrophilic polymer in a dilute aqueous alkaline solution at a pH of not less than about 9 to a cross-linking reaction with divinyl sulfone at about 20° C.

2. A method according to claim 1 wherein the other hydrophilic polymer is a natural or synthetic polysaccharide selected from the group consisting of hydroxyethyl cellulose, carboxymethyl cellulose, xanthan gum, chondroitin sulfate and heparin, a protein selected from the group consisting of collagen, elastin, albumin, a globulin, keratin sulfate, a sulfated aminoglycosaminolgycan and a synthetic water soluble polymer.

3. A method according to claim 1 wherein sodium hyaluronate has a molecular weight of about 50,000 to about $8 \times 10^6$.

4. A method according to claim 1 wherein the combined concentration of sodium hyaluronate and the other hydrophilic polymers in the reaction mixture is 1–8% by weight and the sodium hyaluronate comprises from 5–95% of the total.

5. A method according to claim 1 wherein the ratio of the sodium hyaluronate to divinyl sulfone is from 15:1 to 1:5 by weight.

6. A method according to claim 1 and further comprising adding an alkali metal chloride, sulfate, phosphate or acetate to the reaction mixture in an amount sufficient to provide up to about 20% by weight concentration in the mixture.

7. A method of preparing a cross-linked gel of hyaluronic acid or a mixed cross-linked gel of hyaluronic acid and at least one other hydrophilic polymer having a functional group capable of reacting with divinyl sulfone, either of which further includes an inert water insoluble substance, said method comprising subjecting sodium hyaluronate or a mixture of sodium hyaluronate and said other hydrophilic polymer in a dilute aqueous alkaline solution at a pH of not less than about 9, to which has been added an inert water insoluble substance to a cross-linking reaction with divinyl sulfone at about 20° C.

8. A method according to claim 7 wherein the inert water insoluble substance is a hydrocarbon, an oil or fat, a pigment, polyethylene or polytetrafluoro ethylene.

9. A method according to claim 8 wherein the hydrocarbon is petrolatum, the oil or fat is beeswax, coconut oil or lanolin, and the pigment is kaolin, ferric oxide or an insoluble dye.

10. A method according to claim 7 wherein sodium hyaluronate has a molecular weight of about 50,000 to about $8 \times 10^6$.

11. A method according to claim 7 wherein the concentration of sodium hyaluronate or the mixture of sodium hyaluronate and the other hydrophilic polymer is 1-8% by weight and the inert water insoluble substance is present in an amount of 1-95% by weight based on the total weight of polymers plus inert water insoluble substance.

12. A method according to claim 7 wherein the ratio of the sodium hyaluronate to divinyl sulfone is from 15:1 to 1:5 by weight.

13. A method according to claim 7 and further comprising adding an alkali metal chloride, sulfate, phosphate or acetate to the reaction mixture in an amount sufficient to provide up to about 20% by weight concentration in the mixture.

14. A method of preparing a cross-linked gel of hyaluronic acid or a mixed cross-linked gel of hyaluronic acid and at least one other hydrophilic polymer having a functional group capable of reacting with divinyl sulfone, either of which further includes a low molecular weight substance covalently bonded to the macromolecular network, said method comprising subjecting sodium hyaluronate or a mixture of sodium hyaluronate and said other hydrophilic polymer in a dilute aqueous alkaline solution at a pH of not less than about 9, to which has been added a low molecular weight substance having a functional group with active hydrogen atoms reactive to divinyl sulfone to a cross-linking reaction with divinyl sulfone at about 20° C.

15. A method according to claim 14 wherein the low molecular weight substance is a drug.

16. A method according to claim 14 wherein the low molecular weight substance is a carminic acid.

17. A method according to claim 14 wherein sodium hyaluronate has a molecular weight of about 50,000 to about $8 \times 10^6$.

18. A method according to claim 14 wherein the concentration of sodium hyaluronate or the mixture of sodium hyaluronate and the other hydrophilic polymer is 1-8% by weight and the low molecular weight substance is present in an amount of 1-95% by weight based on the total weight of polymers plus inert water insoluble substance.

19. A method according to claim 14 wherein the ratio of the sodium hyaluronate to divinyl sulfone is from 15:1 to 1:5 by weight.

20. A method according to claim 14 and further comprising adding an alkali metal chloride, sulfate, phosphate or acetate to the reaction mixture in an amount sufficient to provide up to about 20% by weight concentration in the mixture.

21. A mixed cross-linked gel of hyaluronic acid and at least one other hydrophilic polymer having a functional group capable of reacting with divinyl sulfone, wherein the combined concentration of sodium hyaluronate and the other hydrophilic polymer is 1-8% by weight and the sodium hyaluronate comprises from 5-95% of the total.

22. A gel according to claim 21 wherein the other hydrophilic polymer is a natural or synthetic polysaccharide selected from the group consisting of hydroxyethyl cellulose, carboxymethyl cellulose, xanthan gum, chondroitin sulfate and heparin, a protein selected from the group consisting of collagen, elastin, albumin, a globulin, keratin sulfate, a sulfated aminoglycosaminoglycan and a synthetic water soluble polymer.

23. A cross-linked gel of hyaluronic acid or a mixed cross-linked gel of hyaluronic acid and at least one other hydrophilic polymer having a functional group capable of reacting with divinyl sulfone and further comprising an inert water insoluble substance, wherein the concentration of sodium hyaluronate or the mixture of sodium hyaluronate and the other hydrophilic polymer is 1-8% by weight and the inert water insoluble substance is present in an amount of 1-95% by weight based on the total weight of polymers plus inert water insoluble substance.

24. A gel according to claim 23 wherein the inert water insoluble substance is a hydrocarbon, an oil or fat, a pigment, polyethylene or polytetrafluoroethylene.

25. A gel according to claim 24 wherein the hydrocarbon is petrolatum, the oil or fat is beeswax, coconut oil or lanolin, and the pigment is kaolin, ferric oxide or an insoluble dye.

26. A cross-linked gel of hyaluronic acid or a mixed cross-linked gel of hyaluronic acid and at least one other hydrophilic polymer having a functional group capable of reacting with divinyl sulfone and further comprising a low molecular weight substance covalently bonded to the macromolecular network, wherein the concentration of sodium hyaluronate or the mixture of sodium hyaluronate and the other hydrophilic polymer is 1-8% by weight and the low molecular weight substance is present in an amount of 1-95% by weight based on the total weight of the polymer.

27. A gel according to claim 26 wherein the low molecular weight substance is a drug.

28. A gel according to claim 26 wherein the low molecular weight substance is carminic acid.

* * * * *